United States Patent [19]

Higuchi, deceased et al.

[11] Patent Number: 4,845,233

[45] Date of Patent: Jul. 4, 1989

[54] IMIDAZOLIN-2-ONES

[75] Inventors: Takeru Higuchi, deceased, late of Lawrence, Kans., by Martin B. Dickinson, Jr., co-executor; by Kenji W. Higuchi, co-executor, Spokane, Wash.; Ooi Wong, Lawrence, Kans.

[73] Assignee: IPRX, Inc., Lawrence, Kans.

[21] Appl. No.: 96,092

[22] Filed: Sep. 11, 1987

[51] Int. Cl.⁴ .................. C07D 233/70; C07D 233/80
[52] U.S. Cl. ..................................... 548/320; 548/319
[58] Field of Search ................. 548/320, 319; 514/398

[56] References Cited

U.S. PATENT DOCUMENTS 3,356,654 12/1967 Sekmakas ........................... 548/319
4,330,550 5/1982 Lautenschlager et al. ......... 548/320

OTHER PUBLICATIONS

"The Naming and Indexing of Chemical Compounds from Chemical Abstracts", Introduction to the Subject Index of vol. 56, pp. 89N & 91N (1962).

*Primary Examiner*—John M. Ford
*Attorney, Agent, or Firm*—Burns, Doane, Swecker & Mathis

[57] ABSTRACT

A compound having the formula:

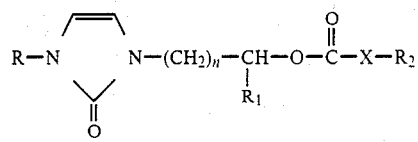

wherein R, $R_1$ and $R_2$ are independently selected from hydrogen; hydroxy; fluorine; bromine; chlorine; $C_1$–$C_{20}$ alkyl; $C_2$–$C_{20}$ alkenyl; $C_2$–$C_{20}$ alkynyl; $C_3$–$C_{10}$ cycloalkyl; $C_2$–$C_{20}$ (monohydroxy or polyhydroxy)alkyl; $C_1$–$C_{20}$ (monohalo or polyhalo)alkyl; carboxy; $C_1$–$C_{20}$ alkylcarboxy; $C_1$–$C_{20}$ alkenylcarboxy; $C_1$–$C_{20}$ carboxyalkyl; $C_1$–$C_{20}$ alkanoyl; $C_1$–$C_{20}$ alkanoyloxy; $C_1$–$C_{20}$ alkoxycarbonyl; carbamoyl; carbamyl; $C_1$–$C_{20}$ alkylcarbamyl; sulfo; $C_1$–$C_{20}$ alkylsulfonyl; $C_1$–$C_{20}$ alkylsulfinyl; $C_1$–$C_{20}$ alkylsulfoxide; $C_1$–$C_{20}$ alkylsulfone; thio; $C_1$–$C_{20}$ alkylthio; amino; nitro; $C_1$–$C_{20}$ alkylamino; $C_1$–$C_{20}$ aminoalkyl; substituted or unsubstituted phenyl or benzyl, the substituents being selected from hydroxy, fluorine, bromine, chlorine, $C_1$–$C_{20}$ alkyl, $C_2$–$C_{20}$ alkenyl, $C_2$–$C_{20}$ (monohydroxy or polyhydroxy)alkyl, X is methyl or oxygen and n is 0 to 20. The invention is also directed to a method for increasing the topical penetration of a physiologically active agent across the skin or membrane of a mammalian organism. Also claimed is a pharmaceutical composition and a novel method for preparing 1-substituted-4-imidazolin-2-one.

6 Claims, 2 Drawing Sheets

IMIDAZOLIN-2-ONES

FIELD OF THE INVENTION

The invention relates to the development of safe and effective agents which improve the rate of percutaneous transport of physiologically active agents. More particularly, the present invention relates to an improved topical penetration enhancer for use in the topical delivery of a local or systemic physiologically active agent to a mammalian organism.

BACKGROUND ART

Dermal drug formulations may represent the oldest drug dosage form in human history. It is highly probable that even ancient people used resins and animal fats to treat damage to the skin resulting from injuries and burns. The use of such dermal formulations for local effect remained largely unchanged until the middle of this century. The concept of administering drugs through the skin to achieve a local or systemic effect was first seriously advocated by Dr. Alejandro Zaffaroni in the early 1970's. Since that time extensive research has been undertaken in this field.

The transdermal route of drug administration offers a number of advantages over the more conventional routes of drug administration. For instance, a drug may be delivered to targeted tissues from adjacent skin areas. The transdermal route of drug administration also allows for a gradual, controlled release of drug into the systemic circulation. Since many drugs are poorly absorbed or delivered through the traditional routes of administration, the transdermal route provides an effective method of achieving improved bioavailability for those drugs. The transdermal route of drug administration is also advantageous since the administration of dermally administered drugs may be easily stopped should an undesirable side effect occur during therapy.

In spite of the foregoing advantages, transdermal formulations are limited. They cannot be used with most polar drugs since they tend to penetrate the skin too slowly. This characteristic is particularly crucial since most drugs are of a polar character. In addition, many drugs elicit a reaction and/or irritation at the site of topical application.

Two methods are known for improving the rate of penetration of polar drugs across the skin. The first method is to make a better formulation of the drug to increase its thermodynamic activity. The thermodynamic activity of a drug in a dermal formulation is dependent on the concentration of the drug and the choice of the vehicle. According to the laws of thermodynamics, the maximum activity of the drug is usually fixed by that of the pure state, i.e., the drug crystal. The second method involves the use of compounds or penetration enhancers to increase the permeability of the barrier membrane. The latter method is generally more practical because of its convenience and effectiveness.

Thus, in the last two decades, a wide variety of compounds have been evaluated as to their effectiveness in enhancing the rate of penetration of drugs through the skin. The classically recognized strong enhancers tend to be proton accepting solvents, e.g., dimethyl sulfoxide (DMSO) and dimethyl acetamide (DMA). Recently, 2-pyrrolidone, N,N-diethyl-m-toluamide (Deet) and 1-dodecylazacycloheptane-2-one (Azone, a registered trademark of Nelson Research), have been reported as effective enhancers. The structure of these compounds are set forth in Table I.

TABLE I

Dimethyl Sulfoxide
(DMSO)

N,N—Dimethyl Acetamide
(DMA)

N,N—Diethyl-m-Toluamide
(Deet)

1-Dodecylazacycloheptane-2-One
(Azone)

2-Pyrrolidone-
5-Carboxylic Acid

2-Pyrrolidone

Several problems have been associated with these prior art dermal enhancers. They cannot be applied to most polar drugs because they tend to penetrate the skin too slowly. And many of these prior art dermal enhancers produce reactions and/or irritation at the site of application.

In the search for new dermal penetration enhancers, Rinta Iubuki in his Ph.D. Thesis in 1985 at the University of Kansas, entitled "Use of Snake Skin as a Model Membrane for Percutaneous Absorption Studies" investigated the use of six compounds for transdermal penetration enhancement of indomethacin in a dosage form of a petrolatum ointment. The compounds disclosed in his thesis are presented below:

R = (CH$_2$)$_6$CH$_3$
R = (CH$_2$)$_9$CH$_3$
R = (CH$_2$)$_{11}$CH$_3$

R$_1$ = (CH$_2$)$_6$CH$_3$
R$_1$ = (CH$_2$)$_9$CH$_3$
R$_1$ = (CH$_2$)$_{11}$CH$_3$

The primary problem with these compounds is their toxicity. Obviously, if a compound when used as a dermal enhancer is either toxic, irritating or allergic, then that compound is unsuitable for application to the human body. DMSO and DMA are also not clinically acceptable for those reasons. Deet and Azone have lower reported toxicities yet their toxicity is high enough such that they are not widely used.

In developing effective dermal enhancers, it would be advantageous to evaluate the potential enhancers by in vivo determination of the rate of human skin penetration of a drug administered along with the enhancer. The amount of drug could be measured in the host's circulation or in the target tissue. Unfortunately, due to the risks involved and the cost of such an evaluation, in vivo determination is not practical. Thus, researchers have used a variety of mammals for in vivo study. Typical mammals include mice, rats, rabbits, pigs and dogs. However, significant differences have been found in the pattern of drug penetration among these mammals and humans. Although the reason for this species variation has not been well-established, the difference in the density of hair follicles is considered to be a factor.

Thus, the disadvantage of in vivo methods has encouraged wide use of various in vitro methods. Copending application U.S. Ser. No. 901,732, filed Aug. 29, 1986, incorporated by reference herein, discloses a novel method for in vitro determination of transdermal absorption. The method involves the use of shed snake skin.

In spite of the numerous attempts in the art to prepare a method for enhancing the absorption of drugs, especially polar drugs, through the skin, there still exists a clear and present need in the art for a method to enhance the absorption of drugs through the skin.

SUMMARY OF THE INVENTION

Surprisingly, the present inventors now find that a novel group of cyclic urea compounds enhance the absorption of active substances through the skin while avoiding the significant pharmacological activities and toxicities of the prior art enhancers. The present invention provides a new class of biodegradable transdermal soft penetration enhancers which because of their structure have less adverse or toxic effects while being excellent promoters of percutaneous adsorption.

The soft penetration enhancer of the present invention is a cyclic urea derivative having the structure:

wherein:

R, R$_1$ and R$_2$ are independently selected from hydrogen; hydroxy; fluorine; bromine; chlorine; C$_1$-C$_{20}$ alkyl; C$_2$-C$_{20}$ alkenyl; C$_2$-C$_{20}$ alkynyl; C$_3$-C$_{10}$ cycloalkyl; C$_2$-C$_{20}$ (monohydroxy or polyhydroxy)alkyl; C$_1$-C$_{20}$ (monohalo or polyhalo)alkyl; carboxy; C$_1$-C$_{20}$ alkylcarboxy; C$_1$-C$_{20}$ alkenylcarboxy; C$_1$-C$_{20}$ carboxyalkyl; C$_1$-C$_{20}$ alkanoyl; C$_1$-C$_{20}$ alkanoyloxy; C$_1$-C$_{20}$ alkoxycarbonyl; carbamoyl; carbamyl; C$_1$-C$_{20}$ alkylcarbamyl; sulfo; C$_1$-C$_{20}$ alkylsulfonyl; C$_1$-C$_{20}$ alkylsulfinyl; C$_1$-C$_{20}$ alkylsulfoxide; C$_1$-C$_{20}$ alkylsulfone; mercapto; C$_1$-C$_{20}$ alkylthio; amino; nitro; C$_1$-C$_{20}$ alkylamino; C$_1$-C$_{20}$ aminoalkyl; substituted or unsubstituted phenyl or benzyl, the substituents being selected from hydroxy, fluorine, bromine, chlorine, C$_1$-C$_{20}$ alkyl, C$_2$-C$_{20}$ alkenyl, C$_2$-C$_{20}$ (monohydroxy or polyhydroxy)alkyl, X is methylene or oxygen and n is 0 to 20. The alkyl, alkenyl and alkynyl groups may be branched or straight chain. The alkenyl and alkynyl groups may have more than one area of unsaturation.

The present invention is also a method for carrying physiologically active agents through body surfaces such as skin and mucous membranes and to compositions for use in that method. More specifically, the invention relates to a method for increasing the penetration of a physiologically active agent across the skin or membrane of a mammalian organism comprising topically applying a physiologically active agent in an amount sufficient to achieve the desired local or systemic effect and the soft penetration enhancing compound described above in an amount sufficient to effectively increase penetration of the physiologically active agent. Also claimed is a pharmaceutical composition comprising same along with a pharmaceutically acceptable carrier therefor.

The present invention is also concerned with the preparation of 1-substituted-4-imidazolin-2-one which is the parent compound for the novel cyclic urea compounds of the present invention.

DESCRIPTION OF THE PREFERRED EMBODIMENTS

The cyclic urea compounds of the present invention may be described as "soft" dermal penetration enhancers since subsequent to exerting their desired effect, they "cleave" via chemical and/or enzymatic hydrolysis to release nontoxic by-products. Without being bound by any particular theory, it is believed that an active ingredient and a soft penetration enhancer are released from a topical formulation and the soft enhancer would then exert its penetration enhancing effect. The soft penetration enhancer, either during or after penetration, would possibly be broken down by skin enzymes, e.g. esterases, into a cyclic unsaturated urea and a fatty acid. In this way, the toxicity of the soft penetration enhancer would be greatly reduced. The possible cleavage of the soft penetration enhancer is set forth below:

As noted earlier, the prior art absorption enhancers have significant pharmacological activities and toxicities. The compounds of the present invention, on the other hand, are a new class of enhancers which because of their structure, do not demonstrate a significant adverse effect on the skin or mucous membranes and yet are excellent promoters of percutaneous absorption. The cyclic urea compounds of the present invention have the formula:

wherein:

R, $R_1$ and $R_2$ are independently selected from hydrogen; hydroxy; fluorine; bromine; chlorine; $C_1$–$C_{20}$ alkyl; $C_2$–$C_{20}$ alkenyl; $C_2$–$C_{20}$ alkynyl; $C_3$–$C_{10}$ cycloalkyl; $C_2$–$C_{20}$ (monohydroxy or polyhydroxy)alkyl; $C_1$–$C_{20}$ (monohalo or polyhalo)alkyl; carboxy; $C_1$–$C_{20}$ alkylcarboxy; $C_1$–$C_{20}$ alkenylcarboxy; $C_1$–$C_{20}$ carboxyalkyl; $C_1$–$C_{20}$ alkanoyl; $C_1$–$C_{20}$ alkanoyloxy; $CI$–$C_{20}$ alkoxycarbonyl; carbamoyl; carbamyl; $C_1$–$C_{20}$ alkylcarbamyl; sulfo; $C_1$–$C_{20}$ alkylsulfonyl; $C_1$–$C_{20}$ alkylsulfinyl; $C_1$–$C_{20}$ alkylsulfoxide; $C_1$–$C_{20}$ alkylsulfone; mercapto; $C_1$–$C_{20}$ alkylthio; amino; nitro; $C_1$–$C_{20}$ alkylamino; $C_1$–$C_{20}$ aminoalkyl; substituted or unsubstituted phenyl or benzyl, the substituents being selected from hydroxy, fluorine, bromine, chlorine, $C_1$–$C_{20}$ alkyl, $C_2$–$C_{20}$ alkenyl, $C_2$–$C_{20}$ (monohydroxy or polyhydroxy)alkyl, X is methylene or oxygen and is n 0 to 20.

Preferably, R is $C_1$–$C_{10}$ alkyl; $R_1$ is hydrogen or methyl; $R_2$ is $C_1$–$C_{20}$ alkyl; X is methyl and n is 0 to 20. More preferably, R is methyl; $R_1$ is hydrogen or methyl; $R_2$ is $C_1$–$C_{20}$ branched chain alkyl; X is methyl and n is 1 to 3. The most preferred compounds are 1-methyl-4-imidazolin-2-one-3 α-ethyl tetradecanoate, 1-methyl-4-imidazolin-2-one-3-isopropylene dodecanoate, and 1-methyl-4-imidazolin-2-one-3propylenedodecanoate.

There are several routes that may be used in the preparation of the cyclic urea compounds of the present invention. The primary route is N-alkylation of the cyclic urea moiety with soft alkylating reagents in chloroform in the presence of sodium hydride as presented below in Reaction Scheme I, wherein Y is halogen and R, $R_1$, $R_2$ and n are as set forth above.

Reaction Scheme I

The reaction is usually conducted at room temperature, however, the temperature may range from about 10° C. to about 200° C. Any organic solvent, including aromatic, aliphatic and aprotic solvents, is suitable in the practice of the present invention. Suitable aromatic solvents include benzene, toluene, xylene, ethyl ether, tetrahydrofuran, and the like. Suitable aliphatic solvents include acetone, chloroform, dichloromethane, carbon tetrachloride and the like. Suitable aprotic solvents include dimethylsulfoxide, dimethylformamide and the like. Any condensation agent may be used as the catalyst. Suitable condensation agents include sodium amide, potassium tertiary butoxide and sodium hydride. Sodium hydride is preferred. Reaction time may range from one hour to several days.

Alternatively, a phase transfer catalysis technique may be used as depicted in Reaction Scheme II wherein R, $R_1$, $R_2$, n, X and Y are as defined above:

Reaction Scheme II

The reaction temperature may range from about 10° C. to about 250° C., however, the reaction is most conveniently conducted at room temperature. Any organic solvent may be used which does not interfere with the reaction. Toluene, benzene and methylene chloride are preferred. Toluene is the most preferred solvent. The reaction mixture is stirred and the reaction time may last anywhere from about three hours to several days. Any phase transfer catalyst may be used in this reaction. Such phase transfer catalysts are known to those of ordinary skill in the art. The preferred phase transfer catalysts are the tetrasubstituted ammonium halides. They are used in an amount sufficient to allow the reaction to proceed. The catalyst preferably used is tetrabutylammonium bromide in an amount of about 0.5 to about 3.0 equivalents. It is also preferred that a base be used during the reaction. Any base is suitable for use in Reaction Scheme II. Preferred bases include KOH and NaOH in an amount of about 0.25 to about five equivalents, generally, about two equivalents are used.

The soft alkylating reagent used in the preparation of the cyclic urea dermal penetration enhancer as set forth in Reaction Scheme II may be prepared by an insertion reaction of a formaldehyde or acetaldehyde group into an alkyl acyl halide by refluxing the corresponding acyl halide and paraformaldehyde or paraldehyde in the presence of zinc chloride or calcium chloride. That reaction is set forth in Reaction Scheme III below where n and $R_2$ are as defined above:

Reaction Scheme III

The reaction is preferably conducted either at room temperature or under reflux. However, the reaction temperature may range anywhere from about 10° C. to about 200° C. The reaction time may extend anywhere from about three hours to about five days. A solvent is not required in Reaction Scheme III, however, optionally any organic solvent may be used. Reaction time generally extends from about two hours to about five days.

Soft alkylating reagents may also be prepared by reaction of the corresponding halo alcohols with an acyl halide in chloroform in the presence of triethylamine as depicted in Reaction Scheme IV below wherein $R_1$, $R_2$, n, X and Y are as defined above:

Reaction Scheme IV

The reaction temperature may be conducted anywhere from about 10° C. to about 200° C., however, room temperature is preferred. Alternatively, the reaction may be conducted at reflux. The use of a solvent is optional. Any organic solvent is suitable. The reaction time generally extends from about one hour to three days. Any base is suitable in Reaction Scheme IV.

Preferred bases include tertiary amines, such as triethylamine; pyridine; and the like.

The carbonate derivatives of the soft dermal penetration enhancers may be prepared according to Reaction Scheme V below where R and $R_2$ are as defined above:

Reaction Scheme V

In Reaction Scheme V, 1-alkyl-4-imidazolin-2-one is reacted with formaldehyde in the presence of sodium hydroxide to give the N-hydroxymethyl product which is condensed with the alkyl chloroformates to yield the carbonate enhancers. In reaction (1) of Reaction Scheme V, any base may be used. Particularly suitable bases include NaOH, KOH, metallic bases and the like. The reaction may be conducted anywhere from about 10° C. to about 200° C., however, room temperature is preferred. Any type of organic solvent may be used in reaction (1), however, protic solvents are preferred. Suitable protic solvents include methanol, ethanol, and the like. Reactions (2) and (3) of Reaction Scheme V may be conducted substantially similar to Reaction Scheme IV.

The present invention is also concerned with a process for the preparation of 1-substituted-4-imidazolin-2-one. This is the building block for the cyclic urea compounds of the present invention. 4-Imidazolin-2-ones have been prepared by acid catalyzed cyclization of aminoacetaldehyde diethyl acetal, however, serious side product formation has made this synthetic approach undesirable. In addition, confirmation of the structure of 1-substituted-4-imidazoline-2-one using that synthetic method was controversial as noted by Duschingsky and Dohn, J. Amer. Chem. Soc., vol. 68, p. 2350 (1956). Leonard and Wiener, J. Amer. Chem. Soc., vol. 98, p. 8218 (1976) reported obtaining an off-white product (50%) by cyclization of N-(2,2-diethoxyethyl)-N-methylurea in the presence of four equivalents of HCl. The present inventors attempted to repeat that synthesis and obtained variable yields of product ranging from a few percent to approximately 20 percent. The product was heavily contaminated with a yellowish side product. The present inventors have now discovered that 1-substituted-4-imidazolin-2-ones may be prepared by acid-catalyzed cyclization of N-(2,2-substituted oxyethyl)-N-substituted ureas to obtain yields of over 90%. The reaction scheme is set forth below:

Reaction Scheme VI wherein R and $R_1$ are independently selected from hydrogen; hydroxy; fluorine; bromine; chlorine; $C_1$-$C_{20}$ alkyl; $C_2$-$C_{20}$ alkenyl; $C_2$-$C_{20}$ alkynyl; $C_3$-$C_{10}$ cycloalkyl; $C_2$-$C_{20}$ (monohydroxy or polyhydroxy)alkyl; $C_1$-$C_{20}$ (monohalo or polyhalo)alkyl; carboxy; $C_1$-$C_{20}$ alkylcarboxy; $C_1$-$C_{20}$ alkenylcarboxy; $Cl$-$C_{20}$ carboxyalkyl; $C_1$-$C_{20}$ alkanoyl; $C_1$-$C_{20}$ alkanoyloxy; $C_1$-$C_{20}$ alkoxycarbonyl; carbamoyl; carbamyl; $C_1$-$C_{20}$ alkylcarbamyl; sulfo; $C_1$-$C_{20}$ alkylsulfonyl; $C_1$-$C_{20}$ alkylsulfinyl; $C_1$-$C_{20}$ alkylsulfoxide; $C_1$-$C_{20}$ alkylsulfone; mercapto; $C_1$-$C_{20}$ alkylthio; amino; nitro; $C_1$-$C_{20}$ alkylamino; $C_1$-$C_{20}$ aminoalkyl; substituted or unsubstituted phenyl or benzyl, the substituents being selected from hydroxy, fluorine, bromine, chlorine, $C_1$-$C_{20}$ alkyl, $C_2$-$C_{20}$ alkenyl and $C_2$-$C_{20}$ (monohydroxy or polyhydroxy)alkyl.

No catalyst is necessary in the first step of Reaction Scheme VI. Any type of solvent may be used, however, aromatic solvents are preferred. The most preferred aromatic solvent in the first step is benzene. The reaction temperature may range from about 10° C. to about 250° C., however, room temperature is preferred. The reaction mixture is stirred and the reaction time may extend anywhere from about two hours to about three days. The ratio of the reactants generally ranges anywhere from about 1:20 to about 20:1, however, ratios outside that range may be used. Yields of approximately 90% may be achieved.

In the second step of Reaction Scheme VI, the temperature generally ranges from about 10° C. to about 250° C., however, room temperature is preferred. The reaction mixture is stirred and the reaction time may extend from about three hours to about four days. A mineral acid such as hydrochloric acid, sulfuric acid, nitric acid or the like, is used to catalyze the reaction. A sufficient amount of mineral acid to catalyze the reaction is used. Suitable amounts include about 0.25 to about 6.0 equivalents and about 2.0 equivalents are preferred. Any organic solvent may be used in this step, but an aromatic solvent such as methanol is preferred. Yields greater than 93% may be achieved in this manner. While not being bound by any method of action, a possible mechanism for the cyclization step is set forth below:

The amount of the cyclic urea dermal penetration enhancer which may be used in the present invention is an effective, non-toxic amount for enhancing absorption either through the skin or mucous membranes. Generally, this amount ranges from about 1 to about 95 weight percent of the topical composition. Preferably, about 0.5 to about 40 weight percent of the penetration enhancer is used in the composition.

The compounds described herein are useful in improving percutaneous absorption of physiologically active agents. The term "physiologically active agent" is used herein to refer to a broad class of useful chemical and therapeutic agents including physiologically active steroids, antibiotics, antifungal agents, antibacterial agents, antineoplastic agents, analgesics and analgesic combinations, anorexics, anthelmintics, antiarthritics, antiasthma agents, anticonvulsants, antidepressants, antidiabetic agents, antidiarrheals, antihistamines, anti-inflammatory agents, antimigraine preparations, antimotion sickness, antinauseants, antiparkinsonism drugs, antipruritics, antipsychotics, antipyretics, antispasmodics, including gastrointestinal and urinary; anticholinergics, sympathomimetics, xanthine derrivatives, cardiovascular preparations including calcium channel blockers, beta-blockers, antiarrhythmics, antihypertensives, diuretics, vasodilators including general, coronary, peripheral and cerebral; central nervous system stimulants, cough and cold preparations, decongestants, hormones, hypnotics, immunosuppressives, muscle relaxants, parasympatholytics, parasympathomimetics, psychostimulants, sedatives, tranquilizers, allergens, antihistaminic agents, anti-inflammatory agents, ultraviolet screening agents, perfumes, insect repellants, hair dyes, and the like. The term "physiologically active" in describing the agents contemplated herein is used in a broad sense to comprehend not only agents having a direct pharmacological effect on the host but also those having an indirect or observable effect which is useful in the medical arts, e.g. the coloring or opacifying of tissue for diagnostic purposes, the screening of U.V. radiation from the tissues and the like.

For instance, typical fungistatic and fungicidal agents include thiabendazole, chloroxine, amphotericin, candicidin, fungimycin, nystatin, chlordantoin, clotrimazole, ethonam nitrate, miconazole nitrate, pyrrolnitrin, salicylic acid, fezatione, ticlatone, tolnaftate, triacetin, zinc, pyrithione and sodium pyrithione.

Steroids include cortisone, cortodoxone, fluoracetonide, fludrocortisone, difluorsone diacetate, flurandrenolone acetonide, medrysone, amcinafel, amcinafide, betamethasone and its esters, chloroprednisone, clorcortelone, descinolone, desonide, dexamethasone, dichlorisone, diflupednate, flucloronide, flumethasone, flunisolide, fluocinonide, flucortolone, fluorometha-lone, fluperolone, fluprednisolone, meprednisone, methylmeprednisolone, paramethasone, prednisolone and prednisone.

Antibacterial agents include sulfonamides, penicillins, cephalosporins, penicillinase, erythromycins, lincomycins, vancomycins, tetracyclines, chloramphenicols, streptomycins, and the like. Specific examples of antibacterials include erythromycin, erythromycin ethyl carbonate, erythromycin estolate, erythromycin glucepate, erythromycin ethylsuccinate, erythromycin lactobionate, lincomycin, clindamycin, tetracycline, chlortetracycline, demeclocycline, doxycycline, methacycline, oxytetracycline, minocycline, and the like.

Other agents include iododeoxyuridine, podophylline, theophylline, isoproterenol, triamicinolone acetonide, hydrocortisone, indomethacin, phenylbutazone paraaminobenzoic acid, aminoprionitrile and penicillamine.

The foregoing list is by no means intended to be exhaustive and any physiologically active agent may be applied by the method of the present invention.

An important advantage of the present invention is that absorption of polar bioactive agents as well as nonpolar drugs is also improved. The polar bioactive agents encompass a variety of therapeutic agents such as the xanthines, triamterene and theophylline, the antitumor agents, 5-fluorouridinedeoxyriboside, 6-mercaptopurine-deoxyriboside, vidarabine, the narcotic analgesics, hydromorphone, cyclazine, pentazocine, bupomorphine, the compounds containing organic anions, heparin, prostaglandins and prostaglandin-like compounds, cromolyn sodium, carbenoxolone, the polyhydroxylic compounds, dopamine, dobutamine, 1-dopa, $\alpha$-methyldopa, the polypeptides, angiotensin antagonists, bradykinin, insulin, ACTH, enkaphaline, endorphin, somatostatin, secretin and miscellaneous compounds such as tetracyclines, tromocriptine, lidocaine, cimetidine or any related compounds. The quantity of these polar bioactive agents necessary for preparing the drug form could vary over a wide range, but would normally be regulated by that quantity necessary to comprise the therapeutically effective dosage form.

Agents normally applied as eye drops, ear drops or nose drops or into the membranes of the oral cavity are also more effective when applied along with the cyclic urea penetration enhancers of the present invention.

As indicated earlier, agents used in diagnosis may be used more effectively when applied dissolved in one of the vehicles of this invention. Patch tests to diagnose allergies may be effected promptly without scratching the skin or covering the area subjected to an allergen when the allergens are applied along with the enhancers of this invention.

This invention is also useful in topical application of cosmetic or esthetic agents. For example, compounds such as melanin-stimulating hormone (MSH) or dihydroxy acetone and the like are more effectively applied to skin to simulate a suntan when they are applied along with the enhancers of this invention. The agent is carried into the skin more quickly and in greater quantity when applied in accordance with this invention. Hair dyes also penetrate more completely and effectively when dissolved n one of the vehicles of this invention.

While the foregoing discussion describes the simultaneous administration of the physiologically active agent along with the penetration enhancer, the penetration enhancer may be applied before or after to the application of the physiologically active agent, if desired.

The physiologically active agents intended for use in the practice of the present invention are intended for either their systemic effect or for their local effect.

Dosage forms for topical application to the skin or other membranes of humans and animals include creams, lotions, gels, ointments, suppositories, sprays, ex. nasal sprays, aerosols, buccal and sub-lingual tablets and any one of a variety of transdermal devices for use in the continuous administration of systemically active drugs by absorption through the skin, oral mucosa or other membranes, see for example, one or more of U.S. Pat. Nos. 3,598,122, 3,598,123, 3,731,683, 3,742,951, 3,814,097, 3,921,636, 3,971,995, 3,993,072, 3,993,073, 3,996,934, 4,031,894, 4,060,084, 4,069,307, 4,201,211, 4,230,105, 4,292,299 and 4,292,303. U.S. Pat. No. 4,077,407. The foregoing patents also disclose a variety of specific systemically active agents which may also be useful in transdermal delivery, which disclosures are hereby incorporated herein by reference.

The usual pharmaceutical compounding agents, diluents or carriers may be included in these compositions as desirable for the particular route of administration and dosage form. The amount and type of diluent or carrier used should, of course, be consistent with the compatability of the agent in the cyclic urea compound of this invention. For instance, a cosolvent or other standard adjuvant, such as a surfactant, may be necessary to maintain the agent in solution or suspension at the desired concentration.

For nasal sprays and other mucous membrane applications isotonic saline may be preferable as a diluent. The cyclic urea enhancer may be present in these forms in various concentrations, for example, from about 2% to about 75% by weight or higher.

Lotions and gels, ointments or creams, may contain the usual ingredients to provide a base, as for example cetyl alcohol, an emulsifier such as lauryl sulfate and water. Another base may be formulated by combining equal weight amounts of stearic acid, cetyl alcohol, triethanolamine and glycerol monostearate with water. Still other bases may utilize polyethylene glycols of different viscosities, depending upon the desired consistency.

A suppository form may be made from a high viscosity polyethylene glycol 4000, water and the cyclic urea penetration enhancer.

Typical inert carriers which may be included in the foregoing dosage forms include conventional formulating material, such as, for example, water, acetone, isopropyl alcohol, freons, ethyl alcohol, polyvinyl pyrrolidone, propylene glycol, fragrances, gel-producing materials such as "Carbopol", mineral oil, stearyl alcohol, stearic acid, spermaceti, sorbitan monooleate, "Polysorbates", "Tweens", sorbital, methylcellulose, and the like. The compositions of the present invention are formulated with any suitable nontoxic pharmaceutically acceptable inert carrier material. Such carrier materials are well known to those skilled in the art of pharmaceutical formulations. For those not skill in the art, reference is made to the text entitled, "REMINGTON'S PHARMACEUTICAL SCIENCES".

Any type of transdermal drug delivery system is also suitable in the practice of the present invention, for instance, the transdermal patch. A variety of transdermal drug delivery systems are disclosed and described in U.S. Pat. No. 4,624,665, herein incorporated by reference.

The amount of the composition, and thus of the physiologically active agent therein, to be administered will obviously be an effective amount for the desired result expected therefrom. This, of course, will be ascertained by the ordinary skill of the practitioner. Due to enhanced activity which is achieved, the dosage of the physiologically active agent may often be decreased from that generally applicable. In accordance with the usual prudent formulating practices, a dosage near the lower end of the useful range of the particular agent may be employed initially and the dosage increased as indicated from the observed response, as in the routine procedure of the physician.

The concentration of physiologically active agent in the various dosage forms is, of course, commensurate with that normally utilized for the particular agent in conventional formulations for effective results for the intended route. Both the amount of physiologically active agent and the amount of penetration enhancer will be influenced by the type of effect desired. To a certain degree, if a more localized effect is required, as for example, in treating a superficial infection with an antibacterial agent, lower amounts of physiologically active agents and lower concentrations of enhancer may be called for. Where deeper penetration is desired, as in the case of local anaesthesia, a higher concentration of enhancer may be desirable to promote adequate penetration. Where general systemic concentration of an agent is desired for a topical preparation, generally higher concentrations of enhancer are desirable and the amount of agent as, for example, a steroid, may be included in the composition sufficient to provide the blood level desired.

In order to further illustrate the present invention and the advantages thereof, the following specific examples are given, it being understood that same are intended only as illustrative and in nowise limitative.

EXAMPLE 1

Procedure Used for the Preparation and Characterization of the Cyclic Urea Dermal Penetration Enhancers (a) Materials and Solvents Chloroform, benzene, toluene, triethylamine and paraldehyde were dried over a molecular sieve before use. 2-Bromoethanol, 3-bromopropanol, 1-bromo-2-propanol, the acyl halides and chloromethylpivalate were obtained from a commercial source and used without further treatment. Sodium hydride was obtained in a 50% suspension in mineral oil and the mineral oil was removed by washing the suspension with dry benzene. Azone was obtained from Nelson Research and indomethacin was obtained from a commercial source.

(b) Apparatus and Structure Characterization

Each compound synthesized was characterized by proton nuclear magnetic resonance spectroscopy, infrared and mass spectroscopy. The purity of the soft enhancer was checked by thin layer chromatography using chloroform or ethyl acetate as the developing solvent system and iodine as the visualizing reagent. Further confirmation of the purity was carried out by HPLC analysis. Because the compound had no ultraviolet absorption, a high performance liquid chromatogram was obtained at 220 nm using a reverse phase column (466 mm×10 cm, RP-18 Spheri 5) in conjunction with a guard tube OD-GU (both purchased from Brownlee Labs) and a mixture of acetonitrile and water as the eluant system. Purification of the soft enhancer was conducted using silica gel (60–200 mesh). To purify the soft alkylating reagents, Florisil was used as the supporting material during liquid column chromatography and chloroform or ethyl acetate were used as the solvent.

Proton nuclear magnetic resonance spectra was recorded on a Varian T-60 spectrometer using $CDCl_3$ and $CCl_4$ as the solvent, infrared spectra on a Beckman spectrophotomer, and mass spectra was conducted using the mass spectroscopy laboratory of the Department of Chemistry, University of Kansas. The melting point was measured on a Thomas Hoover melting apparatus with an uncorrected thermometer. Thin layer chromatagrams were obtained using Analtech HPTLC silica gel tlc plates. HPL chromatograms were obtained by using an Altex pump model 110A and a Kratos Spectroflow 783 programmable absorbance detector.

EXAMPLE 2

Preparation of N-(2,2-Dimethoxyethyl)-N-Methylurea

A solution of aminoacetaldehyde dimethylacetal (25 gm, 0.238 mol in 70 ml of benzene) was cooled in an ice-bath and stirred with a magnetic stirrer. To the solution was added dropwise, a solution of methylisocyanate (13.6 gm in 70 ml of benzene). After the addition was complete, the reaction mixture was stirred at room temperature overnight followed by the removal of the solvent to give a liquid product (35 gm, 90%), tlc and $^1H$ n.m.r. showed the absence of starting material. $^1H$ n.m.r.($CDCl_3$): $\delta 2.85$(3H, d, J=6 Hz, $CH_3NH$), 3.43(2H, t, J=6 Hz, $CH-CH_2NH$), 3.51(6H, s, $CH_3O$), 4.53(1H, t, J=6 Hz, $CH-CH_2$), 5.86(2H, broad, complex multiplets, $D_2O$ exchanged, NHCONH).

EXAMPLE 3

Preparation of 1-Methyl-4-imidazolin-2-one

N-(2,2-Dimethoxyethyl)-N-methylurea (27.5 g, 0.17 mole) was dissolved in a mixture of methanol (670 ml) and water (340 ml). A solution of 0.48 M HCl (400 ml) was added dropwise from a dropping funnel. After stirring the reaction mixture for 3 days, it was neutralized with dilute NaOH solution. The pH of the solution was maintained neutral during the removal of the solvent by a rotovap under reduced pressure until a dry white solid remained in the flask. The solid was extracted four times with chloroform and the combined extracts were dried over anhydrous magnesium sulfate. Removal of the solvent gave 1-methyl-4-imidazolin-2-one (15.5 g, 93%), mp 140–142° C. (sublimed). $^1H$ n.m.r. ($CDCl_3$): $\delta 3.27$(3H, s, $CH_3$-N), 6.50(1H, t, J=2 Hz, HC=CH), 6.63(1H, t, J=2 Hz, HC=CH). ($d_6$-DMSO): $\delta 3.11$(3H, s, $CH_3N$); 6.30(1H, t, J=2 Hz, HC=CH); 6.38(1H, t, J=2 Hz, HC=CH); 11.67(1H, s, broad, NH, $D_2O$ exchanged). $\nu_{max}$(KBr): 1680(C=O; 1610, 1580 $cm^{-1}$(C=C). m/e 98, $C_4H_6N_2O$ requires 98. HPLC $R_t$ 3.10 min. TLC $R_f$ value=0.08.

EXAMPLE 4

Preparation of 1-methyl-4-imidazolin-2-one

The procedure for the present Example was the same as that described in Example 3. N-(2,2-Diethoxyethyl)-N-methylurea (21.3 g, 0.11 mole) was dissolved in a mixture of methanol (520 ml) and water (260 ml) and a solution of 0.48 M HCl (310 ml) was stirred at room temperature for 2 days (TLC showed that the reaction was complete at 30 hours). The usual work-up described in the previous Example gave 1-methyl-4-imidazolin-2-one (10.5 g, 95%).

EXAMPLE 5

Preparation of 1-Ethyl-4-imdazolin-2-one

N-(2,2-dimethoxyethyl)-N-ethylurea (10 g, 0.057 mole) was dissolved in a mixture of methanol (240 ml) and water (115 ml) and a solution of 0.48 M HCl (133 ml) was stirred at room temperature. The reaction was followed by TLC and found to be complete after 20 hours. After stirring the reaction mixture for an additional 4 hours, the work-up described above gave 1-ethyl-4-imidazolin-2-one (5.8 g, 91%), mp 124°–126° C. $^1$H n.m.r.(CCl$_4$): $\delta$1.97(3H, t, J=7 Hz, CH$_3$CH$_2$-N), 3.60(2H, q, J=7 Hz, CH$_3$CH$_2$-N), 6.07(1H, t, J=2 Hz, HC=CH), 6.23(1H, t, J=2 Hz, HC=CH). Signal for the NH was not observed in the spectrum. (d$_6$-DMSO): $\delta$1.67(3H, t, J=7 Hz, CH$_3$$_{CH2}$N); 3.53(2H, q, J=7 Hz, CH$_3$CH$_2$N); 6.30(1H, t, J=2 Hz, HC=CH); 6.42(1H, t, J=2 Hz, HC=CH); 11.67(1H, s, broad, NH, D$_2$O exchanged). $\upsilon_{max}$(KBr): 1670(C=O); 1580 cm$^{-1}$(C=C) m/e 112, C$_5$H$_8$N$_2$O requires 112. TLC R$_f$ $_{value}$=0.16.

EXAMPLE 6

Comparison of Yields of 1-Methyl-4-imidazolin-2-one

1-Methyl-4-imidazolin-2-one was prepared under different reaction conditions in the same manner as presented in Examples 3,4 and 5 above. Table II sets forth the results:

TABLE II

| Run No. | Equivalents of HCl | Yields a | Yields b |
|---|---|---|---|
| 1 | 0.5 | 19$^c$ | 13$^c$ |
| 2 | 1.0 | 29$^c$,38$^d$ | 41$^c$,56$^d$,85$^e$ |
| 3 | 2.0 | 25$^c$,96$^e$,95$^e$ | 93$^e$,93$^e$ |
| 4 | 3.0 | 12$^c$ | 91$^e$ |
| 5 | 4.0 | 18$^c$ | 2$^c$ |
| 6 | 5.0 | — | 2$^c$ |

In column a, the starting material was N-(2,2-diethoxy-ethyl)-N-methylurea. In column b, the starting material was N-(2,2-dimethoxyethyl)-N-methylurea. The symbol c indicates that the product was isolated by concentrating the neutralized reaction mixture and extracting the condensed residue four times with chloroform. The symbol d indicates that the product was isolated by exhaustive extraction of the condensed residue as was done in procedure c with chloroform. The symbol e indicates that the product was isolated by removal of all the solvent from the neutralized reaction mixture to dryness and the solid was then extracted four times with chloroform.

The optimal yield from N-(2,2-diethoxyethyl)-N-methylurea was 29% when 1 equivalent of HCl was used. The low yields are likely attributed to incomplete extraction of 1-methyl-4-imidazolin-2-one. The work-up procedures were carried out to remove as much solvent as possible from the neutralized reaction mixture followed by extracting the concentrated solution with chloroform, resulting in incomplete extraction. However, if the reaction mixture was extracted exhaustively with chloroform, the yields are increased significantly as noted in Run No. 2. In this regard it would be advantageous to remove all the solvent from the reaction mixture to dryness and extract the target compound from the solid residue. By doing this, the yields may be increased to over 90%.

The amount of HCl used in the reaction mixture appears to be important in this type of cyclization. If insufficient HCl is used as in Run No. 1, the yield was lower probably due to incomplete reaction. However, increasing the amount of HCl caused a more yellowish side product to be formed. The reaction mixture turned deep yellow even before the isolation of the product was carried out, especially when N-(2,2-diethoxyethyl)-N-methylurea was used as the starting material. The formation of the yellowish side product is less serious in the case of N-(2,2-dimethoxyethyl)-N-methylurea and can be kept to a minimum by maintaining the pH of the reaction mixture near neutral during the course of isolation of the product.

EXAMPLE 7

Synthesis of 1-Methyl-4-imidazolin-2-one-3-methylenepivalate

1-Methyl-4-imidazolin-2-one (44 mg, 4.4×10$^{-4}$ mol) and sodium hydride (20 mg) in dry benzene (20 ml) was stirred at room temperature for 2 hours. Chloromethylpivalate (71 mg) was added to the suspension and the reaction mixture was stirred for an additional 4 hours. After filtering the reaction mixture through filter paper, the filtrate was concentrated to give a liquid residue which was chromatographed through a column of silica gel to give a pure product (27 mg). T.l.c. Rf value was 0.77 using chloroform as the developing solvent system. $^1$H n.m.r.(CDCl$_3$): $\delta$1.20(9H, s, C[CH$_3$]$_3$); 3.23(3H, s, CH$_3$-N); 5.55(2H, s, —NCH$_2$—O); 6.10 (1H, d, HC=CH); 6.38(1H, d, HC=CH). $\nu_{max}$ (film): 3190, 3150(NH); 1735, 1705(C=O); 1130 cm$^{-1}$(C-O-C). m/e 212, C$_{10}$H$_{16}$N$_2$)O$_3$ requires 212.

EXAMPLE 8

Synthesis of 1-Chloroethyltetradecanoate

Tetradecanoyl chloride (40 gms, 0.16 mol), dry paraldehyde (21 gm, 0.16 mol) and anhydrous calcium chloride (2 gms) were refluxed in a 500 ml one-necked flask (protected from atmospheric moisture with a drying guard tube) for 24 hours. The reaction mixture was cooled and chromatographed through a column of Florisil using chloroform as the eluent to give a semi-solid product (26 gm, 56%). $^1$H n.m.r.(CDCl$_3$): $\delta$0.90(3H, t, J=4 Hz, CH$_3$—), 1.26(22H, s, broad, —[CH$_2$]$_{11}$—), 1.78(3H, d, J=6 Hz, —CHCH$_3$—), 2.33(2H, d, J=6 Hz, —COCH$_2$—), 6.55(1H, q, J=6 Hz, —CHCH$_3$—).

EXAMPLE 9

Synthesis of 1-Methyl-4-imidazolin-2-one-3-α-ethyltetradecanoate

1-Methyl-4-imidazolin-2-one (5 gms, 0.051 mol) and 1-chloroethyltetradecanoate (17 gms, 0.064 mol) in 50 ml of dry chloroform were stirred in a dry round bottomed flask. The flask was under a positive pressure of nitrogen. To the solution was added sodium hydride (2.44 gm, obtained by removing the mineral oil of a 50% suspension of sodium hydride with dry benzene) in small portions with the aid of dry benzene. After stirring the reaction mixture overnight, it was filtered through a column of Florisil with chloroform as the eluent. Concentration of the filtrates gave a liquid residue (12.7 gm) which consisted of some starting material, a side product and the target compound. The material was chromatographed through a column of silica gel using chloroform as the solvent system. The front fractions contained the soft alkylating agent and the side product and the latter fractions the target compound (6 gms, 36 %), m.p. 43°–45° C. $^1$H n.m.r.(CDCl$_3$): $\delta$0.88(3H, t, J=4 Hz, CH$_3$), 1.25(20H, s, broad, —[CH$_2$]$_{11}$—), 1.61(3H, t, J=6 Hz, —CHCH$_3$—), 2.26(2H, t, J=6 Hz, —COCH$_2$—), 3.23(3H, s, CH$_3$N), 6.15(1H, d, J=3 Hz, —CH=CH—), 6.32(1H, d, J=3 Hz, —CH=CH—),6.60(1H, q, J=6 Hz, —CHCH$_3$—). When silica gel was used as the supporting material in liquid chromatography, the particle size of the material was a factor affecting the separation efficiency. It was determined that mesh 60–200 produced a better product than mesh having a larger particle size. In most instances, ethyl acetate was a better solvent than the chloroform although the flow rate of the former through the column was slower. The formation of side products may be suppressed by careful addition of the sodium hydride and by using chloroform as the reaction solvent.

EXAMPLE 10

Synthesis of 1-Ethyl-4-imidazolin-2-one-3-α-ethyltetradecanoat

1-Ethyl-4-imidazolin-2-one (1 gm, 0.009 mol) and 1-chloroethyltetradecanoate (2.6 gm, 0.009 mol) were dissolved in 13 ml of dry chloroform and a suspension of sodium hydride in dry benzene (3 ml) was added portionwise. The reaction mixture was stirred at room temperature overnight and was followed by the workup presented in the preceeding examples. After purification by liquid chromatography using silica gel as the supporting material and chloroform as the eluant (EM Silica gel 500 G, 60–200 mesh was used), 1-ethyl-4-imidazolin-2-one-3-α-ethyltetradecanoate was obtained in a yield of 10% (350 mg). $^1$H n.m.r.(CCl$_4$): $\delta$0.90(3H, t, J=5 Hz, CH$_3$[CH$_2$]$_{11}$CH$_2$—); 1.28(22H, s, broad, CH$_3$[CH$_2$]$_{11}$CH$_2$—); 1.30(3H, t, J=7 Hz, CH$_3$CH$_2$N—); 1.61(3H, d, J=6 Hz, —CHCH$_3$—); 2.25(2H, t, J=6 Hz, CH$_3$[CH$_2$]$_{10}$CH$_2$—); 3.60(2H, q, J=6 Hz, CH$_3$CH$_2$N—); 6.10(1H, d, J=3 Hz, HC=CH); 6.23(1H, d, J=3 Hz, HC=CH); 6.43(1H, q, J=6 Hz, CH$_3$CH—). $\nu_{max}$(film): 3200, 3180(HC=CH); 1745, 1705, 1690(C=O); 1250 cm$^{-1}$(C-O-C). m/e+1 367, C$_{21}$H$_{38}$N$_2$O$_3$ requires 366.

EXAMPLE 11

Synthesis of Chloromethyldodecanoate

A mixture of dodecanoyl chloride (10 gm, 0.045 mol), paraformaldehyde (1.35 gm, 0.045 mol) and anhydrous zinc chloride (0.1 gm) was stirred at 95° C. for 8 hr and at 80° C. for 12 hr. The reaction mixture was cooled and chromatographed through a column of activated acidic aluminum oxide (Aldrich) using chloroform as the eluent to give a solid product (5 gm, 45%). $^1$H n.m.r.(CCl$_4$): $\delta$0.90(3H, t, J=4 Hz, CH$_3$[CH$_2$]$_{10}$-); 1.28(18H, s, broad, CH$_3$[CH$_2$]$_9$CH$_2$-); 1.95(2H, t, J=6 Hz, —CH$_2$CO—); 5.65(2H, s, ClCH$_2$O).

EXAMPLE 12

Synthesis of 1-Methyl-4-imidazolin-2-one-3-methylenedodecanoate

1-Methyl-4-imidazolin-2-one (300 mg, 0.003 mol) and sodium hydride (150 mg) were suspended in 10 ml of dry benzene in a dry flask. Chloromethyldodecanoate (0.77 gm, 0.003 mol) was added to the suspension. After the addition was complete, the reaction mixture was stirred at room temperature for 4 hours. The benzene was removed and the residue was taken up with chloroform (40 ml) followed by the addition of 20 ml of water. The chloroform layer was separated and the aqueous phase extracted with chloroform. The combined extracts were dried over anhydrous magnesium sulfate and concentrated to give a solid product. Column chromatography of the solid afforded I-methyl-4-imidazolin-2-one-3-methylenedodecanoate (400 mg, 43%), mp 41–42° C. T.l.c. Rf=0.24 using chloroform as the solvent system. HPLC Rt=5.57 min, acetonitrile(2):water(1), flow rate=2.0 ml/min. Found: C, 66.00; H, 9.40; N, 9.08. Calc for C$_{17}$H$_{30}$N$_2$O$_3$: C, 65.77; H, 9.74; N, 9.02%. $^1$H n.m.r.(CDCl$_3$): $\delta$0.88(3H, t, J=5 Hz, CH$_3$CH$_2$—); 1.35(18H, s, broad, CH$_3$[CH$_2$]$_9$CH$_2$—); 2.30(2H, t, J=6 Hz, —COCH$_2$—); 3.2(3H, s, CH$_3$N—); 5.53(2H, s, —CH$_2$O—); 6.08(1H, d, J=3 Hz, HC=CH); 6.38(1H, d, J=3 Hz, HC=CH). $\nu_{max}$(BKr): 3200, 3160, 3140(HC=CH); 1745, 1705(C=O); 1250 cm$^{-1}$(C-O-C) m/e 310, C$_{17}$H$_{30}$N$_2$O$_3$ requires 310.

EXAMPLE 13

Synthesis of 2-Chloroethyldodecanoate

A mixture of 2-chloroethanol (5 gm, 0.062 mol) and dodecyl chloride (13.5 gm, 0.062 mol) were dissolved in dry dichloromethane (35 ml). The mixture was stirred while a solution of triethylamine (6.26 gm, 0.062 mol) was added dropwise to the mixture. Heat was generated and a solid formed. The reaction mixture was stirred at room temperature for 3 hours and chromatographed through a column of silica gel using chloroform as the eluent. Removal of the solvent afforded a total of 7 gm of product (95%). $\nu_{max}$(film): 1745(C=O); 1165 cm$^{-1}$(C-O-C). $^1$H n.m.r.(CCl$_4$): $\delta$0 90(3H, t, J=4 Hz, CH$_3$—); 1.28(18H, s, broad, CH$_3$[CH$_2$]$_9$—); 1.95(2H, t, J=6 Hz, —CH$_2$CO—); 3.60(2H, t, J=6 Hz, ClCH$_2$CH$_2$O); 4.27(, t, J=6 Hz, ClCH$_2$CH$_2$O).

EXAMPLE 14

Synthesis of 2-Bromoethyldodecanoate

A mixture of 2-bromoethanol (5 gm, 0.04 mol), dodecylchloride (8.7 gm, 0.04 mol) and triethylamine (4 gm, 0.04 mol) in chloroform (40 ml) was stirred at room temperature for 3 hours to give 9 gm of product (73%).

EXAMPLE 15

Synthesis of 1-Methyl-4-imidazolin-2-one-3-ethylenedodecanoate by Phase Transfer Catalysis A mixture of 1-methyl-4-imidazolin-2-one (1.5 gm, 0.015 mol), 2-bromoethyldodecanoate (4.5 gm, 0.015 mol), powdered potassium hydroxide (1.0 gm) and tetrabutylammonium bromide (3.2 gm) was suspended in benzene (70 ml). The reaction mixture was stirred at 60° C. for 4 hours and cooled to room temperature. The reaction mixture was then washed with several portions of water to remove the base and the ammonium bromide. It is possible that improved yields may be obtained by avoiding the use of water. The benzene phase was then dried over anhydrous magnesium sulfate, condensed and chromatographed through a column of silica gel using chloroform as the eluent. A pure fraction of product was obtained (260 mg, 5%) with Rf value of 0.23 on silica gel tlc plates using ethyl acetate as the developing solvent. $^1$H n.m.r.(CCl$_4$): δ0.90(3H, t, J=5 Hz, CH$_3$[CH$_2$]$_{11}$-); 1.26(18H, s, broad, CH$_3$[CH$_2$]$_9$CH$_2$—); 2.25(2H, t, J=6 Hz, CH$_3$[CH$_2$]$_9$CH$_2$—); 3.27(3H, s, CH$_3$N); 3.77(2H, t, J=6 Hz, NCH$_2$CH$_2$O—); 4.23(2H, t, J=6 Hz, NCH$_2$CH$_2$O—); 6.08(1H, d, J=3 Hz, HC=CH); 6.20(1H, d, J=3 Hz, HC=CH). ν$_{max}$(film): 3180, 3150, 3120(HC=CH); 1740, 1680(C=O); 1240, 1170 cm$^{-1}$(C-O-C), m/e 324, C$_{18}$H$_{32}$N$_2$O$_3$ requires 324.

EXAMPLE 16

Synthesis of 3-Bromopropyldodecanoate

A mixture of 3-bromopropyl alcohol (2 gm, 0.014 mol) and dodecyl chloride (3.13 gm, 0.014 mol) and triethylamine (1.4 gm) in dry chloroform (15 ml) was stirred at room temperature for 16 hours to obtain 3.6 gm of product (85%).

EXAMPLE 17

Synthesis of 1-Methyl-4-imidazolin-2-one-3-propylenedodecanoate

A mixture of 1-methyl-4-imidazolin-2-one (1.2 gm, 0.012 mol), 3-bromopropyldodecanoate (3.6 gm, 0.011 mol), powdered potassium hydroxide (0.56 gm) and tetrabutylammonium bromide (3.2 gm) in benzene (60 ml) was stirred at room temperature for 3 days. After the usual work-up, 1-methyl-4-imidazolin-2-one-3propylenedodecanoate (0.4 gm, 10%) was obtained with t.l.c. Rf value 0.18 using ethyl acetate as the developing solvent system; HPLC Rt=3.74 min, acetonitrile(2):water(1), flow rate=3.5 ml/min. $^1$H n.m.r.(CCl$_4$): δ0.90(3H, t, J=4 Hz, CH$_3$CH$_2$—); 1.28(18H, s, broad, CH$_3$[CH$_2$]$_9$CH$_2$—); 1.93(2H, quint, J=7 Hz, —NCH$_2$CH$_2$CH$_2$O—); 2.25(2H, t, J=6 Hz, —CH$_2$CO—); 3.18(3H, s, CH$_3$N—); 3.61(2H, t, J=7 Hz, NCH$_2$CH$_2$CH$_2$O—); 4.07(2H, t, J=7 Hz, NCH$_2$CH$_2$CH$_2$O—); 6.10(2H, s, HC=CH). νhd max(film): 3200, 3160, 3120(HC=CH); 1740, 1690(C=O); 1240 cm$^{-1}$(C-O-C). m/e 338, C$_{19}$H$_{34}$N$_2$O$_3$ requires 338.

EXAMPLE 18

Synthesis of 1-Methyl-4-imidazolin-2-one-3-isopropylenedodecanoate by phase transfer catalysis A mixture of 1-methyl-4-imidazolin-2-one (4 gm, 0.041 mol), 2-chloro-1-methylethyldodecanoate (prepared by reaction of dodecyl chloride with 1-bromo-2-propanol in the presence of triethylamine) (13.1 gm, 0.041 mol), powdered potassium hydroxide (4.6 gm) and tetrabutylammonium bromide (26 gm) in toluene (180 ml) was heated and stirred at 75° C. overnight (24 hours). After the usual work-up, a liquid product was obtained and chromatographed through a column of silica gel (mesh 60-200 using ethylacetate as the eluent). A pure fraction was obtained (2.9 gm, 21%) with t.l.c. Rf value 0.27 using ethyl acetate as the developing solvent system and HPLC Rt 5.90 min, using acetonitrile(2):water(1) as the solvent system, flow rate=3.5 ml/min. Found: C, 67.7; H, 10.4; N, 8.6. Calc for C$_{19}$H$_{34}$N$_2$O$_3$: C, 67.4; H, 10.1; N, 8.3%. $^1$H n.m.r.(CCl$_4$): δ0.90(3H, t, J=5 Hz, CH$_3$CH$_2$—); 1.22(3H, d, J=6 Hz, —CHCH$_3$O—); 1.30(18H, s, broad, CH$_3$[CH$_2$]$_9$CH$_2$—); 2.23(2H, t, J=6 Hz, —CH$_2$CO—); 3.21(3H, s, CH$_3$N—); 3.66(2H, d, J=6 Hz, NCH$_2$—CH—); 5.00(1H, sext, CH$_2$CHCH$_3$—O); 6.06(1H, d, J=3 Hz, HC=CH); 6.17(1H, d, J=3 Hz, HC=CH). ν$_{max}$(film): 3200, 3150, 3120(HC=CH); 1740, 1690(C=O); 1500 cm$^{-1}$(C-O-C). m/e 338, C$_{19}$H$_{34}$N$_2$O$_3$ requires 338.

EXAMPLE 19

Synthesis of 1-Methyl-3-hydroxymethyl-4-imidazolin-2-one

A mixture of 1-methyl-4-imidazolin-2-one (4 gms, 0.04 mol), 20 ml of formaldehyde (37% aqueous solution), sodium hydroxide (100 mg), and 20 ml of methanol was stirred at room temperature for 20 hours. After removing the solvent using a rotovap at reduced pressure, a liquid residue was obtained and filtered through a column of silica gel using chloroform as the eluent. The residue solidified after left standing overnight and was dissolved in water and then extracted with chloroform. The aqueous phase was concentrated and chromatographed through a column of silica gel G 60. Removal of the solvent afforded a solid which upon addition of acetone became white suspension. The solid was washed twice with acetone and air-dried (1.0 gm, 22%) and sublimed at reduced pressure, m.p. 101.5°-103.5° C. Found: C, 46.70; H, 6.18: N, 21.80. Calc. for C$_5$H$_8$N$_2$O$_2$: C, 46.87; H, 6.29; N, 21.86%. $^1$H n.m.r.(CDCl$_3$): δ3.15(3H, s, CH$_3$N—); 5.02(2H, s, broad, N-CH$_2$OH); 5.8(1H, s, broad, OH); 6.1 (1H, d, J=3 Hz, HC-CH); 6.3(1H, d, J=3 Hz, HC=CH). ν$_{max}$(KBr): 3220(OH, broad); 3120, 3100(HC=CH); 1655 cm$^{-1}$(C=O). m/e 128, C$_5$H$_8$N$_2$O$_2$ requires 128.

EXAMPLE 20

Synthesis of 1-Methyl-4-imidazolin-2-one-3-methylenedodecyl carbonate

1-Methyl-3-hydroxymethyl-4-imidazolin-2-one (1.1 gm, 0.009 mol), dodecyl chloroformate (2.3 gm, 0.009 mol) were dissolved in 10 ml dichloromethane. To the solution was added 1.2 ml of triethylamine. The reaction mixture was stirred at room temperature for 10 hours and then treated with 15 ml of water. The organic phase was separated and the aqueous phase was extracted twice with chloroform. The combined extracts were dried over anhydrous magnesium sulfate and concentrated to give a liquid residue which was chromatographed through a column of silica gel G 60 using chloroform as the eluent. A pure fraction was obtained and gave 200 mg of product (6%), m.p. 44°-46° C. m/e 340, C$_{18}$H$_{32}$N$_2$O$_4$ requires 340.

EXAMPLE 21

Preparation of 1-chloroethyllinoleic ester

Linoleoyl chloride (prepared by reaction of linoleic acid with thionyl chloride) (16 gm), paraldehyde (5 gm) and calcium chloride (2 gm) were refluxed for 24 hrs. The reaction mixture was cooled and concentrated and filtered through a column of Florisil. After work-up, 18 gms of product was obtained.

EXAMPLE 22

Preparation of 1-methyl-4-imidazolidin-2-one-3-α-ethyllinoleic ester

1-Methyl-4-imidazolidin-2-one (1 gm, 0.01 mol) and 1-chloroethyllinoleic ester (6 gm) were dissolved in 40 ml of dry chloroform. The solution was stirred while a suspension of sodium hydride (0.24 gm in dry benzene) was added in small portions. The reaction mixture was stirred at room temperature for 4 hrs followed by the removal of solvent under reduced pressure to give a liquid residue which was shown to contain a mixture of compounds. The mixture was chromatographed through a column of silica gel using chloroform as the eluent. A latter fraction of low $R_f$ value (tlc/silica gel/chloroform) was isolated and shown by 1H n.m.r. to contain the target compound. 1H n.m.r. (CDCl$_3$): δ0.90 (CH, t, J=4 Hz, CH$_3$), 1.30(20H, s, broad), 1.63(3H, d, J=6 Hz, —CHCH$_3$—), 2.13 (compiles multiplets), 2.77(2H, t, J=4 Hz, —COCH$_2$—), 3.23(3H, s, CH$_3$N—), 5.33(3H, multiplets), 6.15(1H, d, J=2 Hz, —CH=CH—), 6.31(1H, d, J=2 Hz, —CH=CH—), 6.61(1H, q, J=6 Hz, —CHCH$_3$—).

EXAMPLE 23

Preparation of Ointment for Evaluation

Ointments were prepared by mixing 1% indomethacin, 5% dermal penetration enhancer and 94% petrolatum at 55°–60° C. to give a homogeneous dispersion of indomethacin. In the cases where the enhancers are liquid the indomethacin and the enhancer were first mixed well and then followed by the incorporation of the petrolatum. The mixture was melted at 55°–60° C. and stirred until a homogeneous ointment was obtained. For low melting enhancers, the enhancer and the indomethacin were melted together and mixed in a water-bath followed by the incorporation of petrolatum. For high melting enhancers, it was necessary to mix the components in an agate mortar.

EXAMPLE 24

Preparation and Use of the Black Rat Snake Barrier Membrane to Evaluate Drug Penetration A whole shed snake skin from the molt of adult *Elaphe obsoleta* (black rat snake) was obtained from the Animal Care Unit of the University of Kansas. Only the dorsal side of the shed snake skin was used for in vitro penetration studies. The head and tail sections of the snake skin was removed and the remainder of the skin was cut randomly into sections of approximately 2 inches by 2 inches. Each piece of snake skin was hydrated overnight by first soaking the skin in water (about 5 to 10 min) until it could be stretched and then it was placed on a plastic pan which held some water. The pan was floated on a water-bath of 32° C. overnight.

Approximately 30 mg of ointment as prepared as described in Example 23 was smeared evenly on an area of the 2"×2" snake skin. The ointment was smeared into an essentially circular area approximately 1.77 cm$^2$ and having a diameter of approximately 15 mm. The snake skin was then mounted on top of the receptor cell of a verticle diffusion cell assembly in which a small magnetic bar was inserted and filled with an isotonic buffer. A rubber o-ring was placed on top of the skin followed by the placement of the donor cell. The two cells were clamped together and transferred to a water-bath (32° C.) which had several magnetic stirrers placed underneath to stir the contents of the diffusion cells. Samples from the cells were withdrawn periodically by gravity by inputing fresh isotonic buffer into the cells inlets. The first five drops were discarded and the following four drops were collected for analysis. These nine drops of sample solution were approximately equivalent to about 0.20 ml.

The samples were analyzed for the concentration of indomethacin using either a Spectroflow 783 programmable absorbance detector or a Perkin-Elmer ISS-100 HPLC apparatus with a Perkin-Elmer LC9 UV spectrophotometric detector and a Perkin-Elmer ISS-100 automatic sampler with the detection wavelength set at 260 nm. A reverse phase column, RP-8 Spheri-5, 4.6×100 mm and a guard tube OD-GU, purchased from Brownlee Labs, were used in conjunction with the HPLC system. The flow rate was 1.0 ml/min and the solvent system was a mixture of acetonitrile (50%) and a 0.01M phosphate buffer (pH 3.0) (50%).

The concentration in each sample was interpreted from a standard curve which was obtained by plotting the peak areas obtained from HPL chromatograms versus four different standard solutions of indomethacin. The standard curves were linear over a range of concentrations from 2.5 to 10 ug/ml. The receptor cell volume was calibrated by weighing the amount of water in the cell. The first sample needs no concentration correction. However, the concentration in the subsequent samples can be corrected by the following equation $$\left( \frac{\text{volume withdrawn}}{\text{volume of the receptor cell}} \times X_i \right) + X_{i+1} + Y_i$$

where $x_i$ is a member of microgram of indomethacin in the $i^{th}$ sample. Also, the volume withdrawn for each sampling is about 0.20 ml. $Y_i$ is the concentration correction for i-1 sample.

Runs 1 to 13 in Table III represent various compounds having the basic structure:

TABLE III

Transdermal Data and Yields for Cyclic Urea Dermal Penetration Enhancers Having The Structure Of The Compound Identified Above

| Run No. | Compound | | | | | Relative Penetration (%) | Yield (%) |
|---|---|---|---|---|---|---|---|
| | R | R$^1$ | m | n | X | | |
| 1 | Me | Me | 9 | 1 | CH$_2$ | 120–200 | 21 |
| 2 | Me | Me | 11 | 1 | CH$_2$ | 70 | 20 |
| 3 | Me | Me | 11 | 0 | CH$_2$ | 80–100, 50* | 36 |
| 4 | Me | Me | 9 | 0 | CH$_2$ | 60, 40* | 10 |
| 5 | Me | H | 9 | 2 | CH$_2$ | 100 | 10 |
| 6 | Me | H | 9 | 1 | CH$_2$ | 60 | 5 |
| 7 | Et | Me | 11 | 0 | CH$_2$ | 50 | 10 |
| 8 | Me | H | 11 | 0 | O | 50 | 6 |
| 9 | Me | H | 9 | 0 | O | 15 | 15 |
| 10 | Me | H | 13 | 0 | O | 10 | 10 |
| 11 | Me | H | 7 | 0 | CH$_2$ | 10 | 81 |
| 12 | Me | H | 9 | 0 | CH$_2$ | 10, 20* | 43 |
| 13 | Me | Me | 7 | 1 | CH$_2$ | 50 | 19 |

TABLE III-continued
Transdermal Data and Yields for Cyclic Urea Dermal Penetration Enhancers Having The Structure Of The Compound Identified Above

| Run No. | Compound R | R¹ | m | n | X | Relative Penetration (%) | Yield (%) |
|---|---|---|---|---|---|---|---|
| 14 | Azone | | | | | 100 | — |

The foregoing results were obtained by using 5% of the transdermal penetration enhancer in the ointment. An asterisk (*) indicates that in those runs 10% enhancer was present in the ointment. Thus, Table III primarily reflects the transdermal penetration data of 5% indomethacin from ointments of 94% petrolatum and 5% enhancer. In Run No. 14, Azone was selected as the standard for comparison since it is claimed to be an excellent enhancer although it is too toxic. It has been reported that the intraperitoneal administration of Azone has an $LD_{50}$ of approximately 232 mg/kg. Penetration that was equal to the penetration of Azone was reported as 100% relative penetration. The relative penetration enhancement of the soft enhancers was obtained by dividing the slope of the plot of the amount of indomethacin penetrated versus time of the enhancer by that of Azone. Yield (%) reflects isolated and purified yields.

Figure 1:
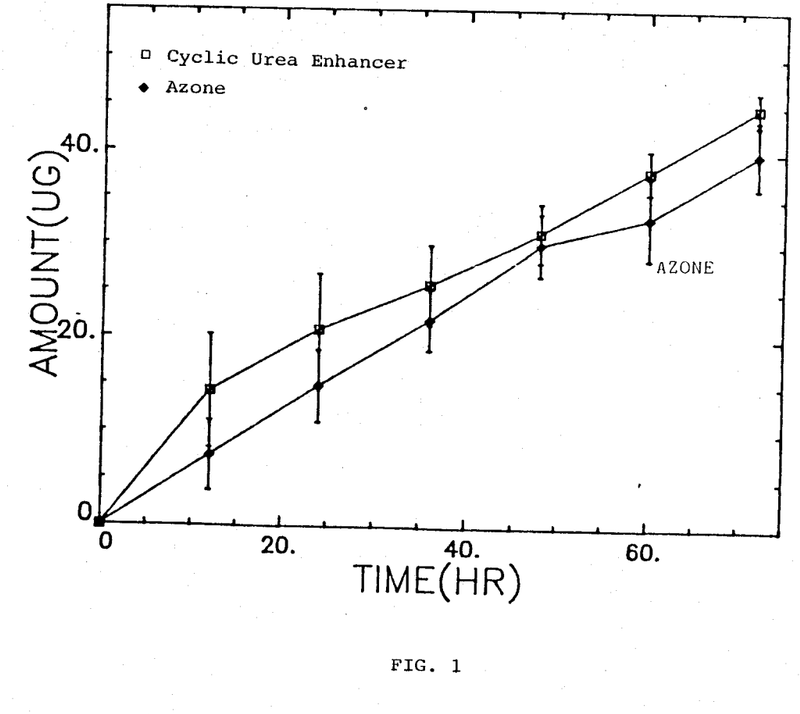
FIG. 1 is a graph of a plot of the amount of indomethacin detected in the donor cell of the verticle diffusion cell versus time. Within the first 24 hours, the penetration enhancement of indomethacin using 1-methyl-4-imidazolin-2-one-3propylene dodecanoate is well above that of the standard Azone.

FIG. 1 reflects the compound of Run No. 1 in comparison to Azone.

Figure 2:
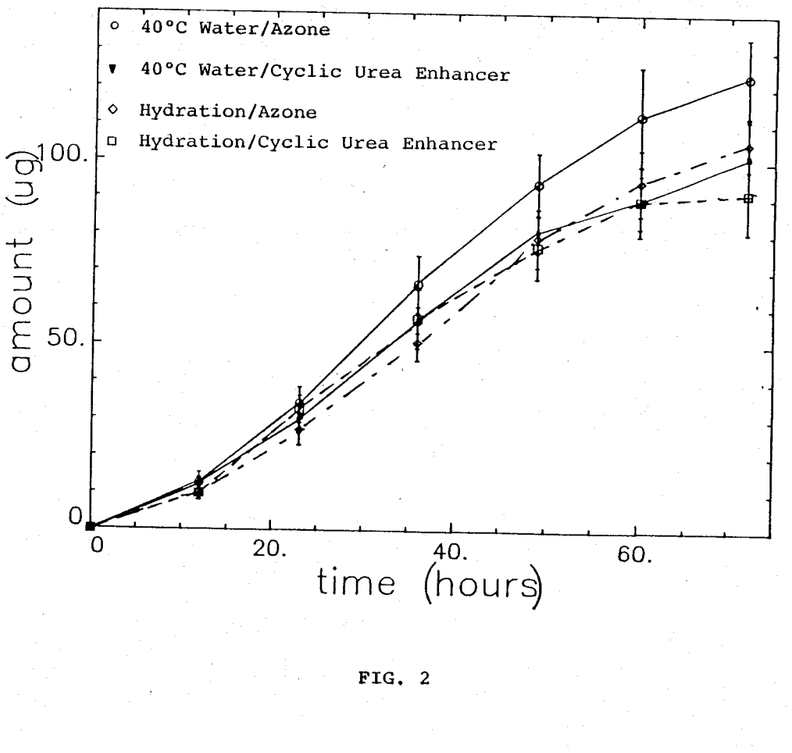
FIG. 2 is a graph of a plot as described in FIG. 1 using 1-methyl-4-imidazolin-2-one-3 α-ethyl tetradecanoate as the penetration enhancer. Four separate runs are depicted.

In FIG. 2 the small circle represents pretreatment of the snake skin by soaking the snake skin in 40° C. water prior to application of 1% indomethacin ointment containing 5% Azone. The triangle represents pretreatment of the snake skin by soaking the snake skin in 40% water prior to application of 1% indomethacin ointment containing 5% of the cyclic urea enhancer. The diamond represents overnight hydration, that is soaking the snake skin in water, prior to application of 1% indomethacin ointment containing 5% Azone. The square represents overnight hydration of the snake skin prior to application of 1% indomethacin ointment containing 5% cyclic urea enhancer.

EXAMPLE 25

Acute Toxicity Study

The compound, 1-methyl-4-imidazolidin-2-one-3-α-ethyl tetradecanote, identified as Run No. 3 in Table III was dispersed in saline (0.85% NaCl in boiled-out deionized water) with 2% Tween 80 (Sigma). Three doses, 100 mg/Kg, 320 mg/Kg and 1000 mg/Kg were injected subcutaneously into three groups of Swiss white mice, weights ranging from 26 to 30 gms. Two samples (200 gm/2.0 ml and 85 mg/3.0 ml) were prepared by dispersing the soft enhancer in a powder form in a 2% Tween 80 saline solution. The dispersion was shaken in a 10 ml weighing bottle in which a plastic ball was placed. Prior to injection the dispersions were shaken and withdrawn into a sterile graduated 1 c.c. TB syringe (readable to 0.05 ml). Sterile hypodermic needles (25.4mm) were required for injecting the higher concentration sample due to coarser dispersion. The control mice (two) were injected with an equivalent volume of saline solution. The mice were observed periodically and did not show any obvious abnormality. The mice survived after seven days. Dissection of the mice injected with the highest dose and the control mice indicated that there is no obvious damage to the internal organs and tissue at the injection site.

EXAMPLE 26

Chronic Toxicity Study

The compound identified in Example 25 and represented as Run No. 3 in Table III, was also evaluated for chronic toxicity. Six Swiss white mice were injected subcutaneously at a dose of 1000 mg/Kg daily for 14 days. A sample dispersion of 400 mg/4.0 ml was prepared by dispersing the soft enhancer in a powder form in a 2% Tween 80 saline solution. The homogeneous dispersion was obtained by vortexing the material in a conical flask in which a plastic ball was placed. Sample dispersion was prepared alternative day in order to avoid serious contamination. Prior to injection the dispersion was shaken and withdrawn into a sterile graduated 1 cc TB syring (readable to 0.05 ml). Sterile hypodermic needles (25.4 mm) were required for injecting the dispersion. The control mice were injected an equivalent volume of the 2% Tween 80 suspension in saline. The suspension was prepared on an alternative day to avoid serious contamination. All mice survived after 15 days. Two mice injected with the sample and one from the control were sacrificed and dissected for examination. For the control mouse, there was no obvious damage to the tissue and the internal organs. However, a substantial amount of yellowish material was found on the injection site of the mice but no obvious damage to the internal organs was seen. The mice were maintained for a period of 39 days during which time one mouse was sacrificed to check for the presence of the yellowish material. The yellowish material disappeared after 39 days.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A compound having the formula:

wherein: R, R₁ and R₂ are independently selected from hydrogen; hydroxy; fluorine; bromine, chlorine; $C_1$-$C_{20}$ alkyl; $C_2$-$C_{20}$ alkenyl; $C_2$-$C_{20}$ alkynyl; $C_3$-$C_{10}$ cycloalkyl; $C_2$-$C_{20}$ (monohydroxy or polyhydroxy)alkyl; $C_1$-$C_{20}$ (monohalo or polyhalo)alkyl; carboxy; $C_1$-$C_{20}$ alkylcarboxy; $C_1$-$C_{20}$ alkenylcarboxy; $C_1$-$C_{20}$ carboxyalkyl; $C_1$-$C_{20}$ allkanoyl; $C_1$-$C_{20}$ alkanoyloxy; $C_1$-$C_{20}$ alkoxycarbonyl; carbamoyl; carbamyl; $C_1$-$C_{20}$ alkylcarbamyl; sulfo; $C_1$-$C_{20}$ alkylsulfonyl; $C_1$-$C_{20}$ alkylsulfinyl; $C_1$-$C_{20}$ alkylsulfoxide; $C_1$-$C_{20}$ alkylsulfone;

mercapto; $C_1$–$C_{20}$ alkylthio; amino; nitro, $C_1$–$C_{20}$ alkylamino; $C_1$–$C_{20}$ aminoalkyl; substituted or unsubstituted phenyl or benzyl, the substituents being selected from hydroxy, fluorine, bromine, chlorine, $C_1$–$C_{20}$ alkyl, $C_2$–$C_{20}$ alkenyl, $C_2$–$C_{20}$ (monohydroxy or polyhydroxy)alkyl, X is methyl or oxygen and n is 0 to 20.

2. The compound as claimed in claim 1, wherein R is $C_1$–$C_{10}$ alkyl; $R_1$ is hydrogen or methyl; $R_2$ is $C_1$–$C_{20}$ branched or straight chain alkyl; X is methyl and n is 0 to 20.

3. The compound as claimed in claim 2, wherein R is methyl; $R_1$ is hydrogen or methyl; $R_2$ is $C_1$–$C_{20}$ branched or straight chain alkyl; X is methyl and n is 1 to 3.

4. The compound as claimed in claim 1, being 1-methyl-4-imidazolin-2-one-3α-ethyl tetradecanoate.

5. The compound as claimed in claim 1, being 1-methyl-4-imidazolin-2-one-3-isopropylene dodecanoate.

6. The compound as claimed in claim 1, being 1-methyl-4-imidazolin-3-propylenedodecanoate.

* * * * *